US008529449B2

(12) United States Patent
    Patch

(10) Patent No.: US 8,529,449 B2
(45) Date of Patent: Sep. 10, 2013

(54) METHOD AND SYSTEM OF THERMOACOUSTIC COMPUTED TOMOGRAPHY

(75) Inventor: Sarah K. Patch, Milwaukee, WI (US)

(73) Assignee: General Electric Company, Schenectady, NY (US)

( * ) Notice: Subject to any disclaimer, the term of this patent is extended or adjusted under 35 U.S.C. 154(b) by 2809 days.

(21) Appl. No.: 10/800,957

(22) Filed: Mar. 15, 2004

(65) Prior Publication Data

US 2005/0203370 A1    Sep. 15, 2005

(51) Int. Cl.
    *A61B 8/00*    (2006.01)
(52) U.S. Cl.
    USPC ............... 600/438; 378/4; 600/407; 600/425
(58) Field of Classification Search
    USPC ............... 600/407, 437–438, 443, 444, 445, 600/448; 606/2, 20, 27, 32; 374/6, 7
    See application file for complete search history.

(56) References Cited

U.S. PATENT DOCUMENTS

| | | | |
|---|---|---|---|
| 5,121,629 A * | 6/1992 | Alba | 73/61.41 |
| 5,713,356 A | 2/1998 | Kruger | |
| 6,102,857 A | 8/2000 | Kruger | |
| 6,104,942 A | 8/2000 | Kruger | |
| 6,181,832 B1 * | 1/2001 | Maas, III | 382/294 |
| 6,216,025 B1 | 4/2001 | Kruger | |
| 6,292,682 B1 | 9/2001 | Kruger | |
| 6,490,470 B1 | 12/2002 | Kruger | |
| 2002/0065455 A1 * | 5/2002 | Ben-Haim et al. | 600/407 |
| 2007/0140541 A1 * | 6/2007 | Bae et al. | 382/131 |

FOREIGN PATENT DOCUMENTS

| | | | |
|---|---|---|---|
| JP | 63211879 A | * | 9/1988 |
| JP | 2000-052634 A | | 2/2000 |

OTHER PUBLICATIONS

Kruger RA et al. "Breast Cancer in Vivo: Contrast Enhancement with Thermoacoustic CT at 434 MHz—Feasibility Study", *Radiology 2000*; 216:279-283.
Kruger RA et al., "Thtermoacoustic CT with Radio Waves: A Medical Imaging Paradigm", *Radiology 1999*; 211:275-278.
Kruger RA et al., "Thermoacoustic Computed Tomography—Technical Considerations", *Medical Physics 1999*; 26(9):1832-1837.
Joines WT et al., "The Measured Electrical Properties of Normal and Malignant Human Tissues from 50 to 900 MHz", *Medical Physics 1994*; 21(4):547-550.
Patch SK, "Thermoacoustic Tomography—Consistency Conditions and the Partial Scan Problem", *Phys. Med. Biol. 2004*; 49:2305-2315.

(Continued)

*Primary Examiner* — Elmer Chao
(74) *Attorney, Agent, or Firm* — Ziolkowski Patent Solutions Group, SC

(57) ABSTRACT

The present invention is a directed to method and system of TCT imaging whereupon data associated with unmeasured or inadmissible transducer locations is determined from data acquired at measured or admissible transducer locations. The invention analyzes measured TCT data associated with several transducer locations to provide an estimate of unmeasured data so as to complete a full data set for image reconstruction. In this regard, by measuring TCT data at many points on the surface of a hemispherical bowl or sphere in which an imaging object is placed, mathematical coefficients may be determined for the TCT data as a function of transducer location. From these coefficients, the unmeasured transducer locations may be evaluated such that data associated with the unmeasured transducer locations may be estimated and utilized for image reconstruction to improve image quality as well as improve the diagnostic sensitivies or capabilities of the TCT system.

14 Claims, 2 Drawing Sheets

(56) References Cited

OTHER PUBLICATIONS

Finch D et al., "Determining a Function From Its Mean Values Over a Family of Spheres", *SIAM Journal of Mathematical Analysis 2004*; 35(5):1213-1240.

Louis AK et al., "Local Tomographic Methods in SONAR", pp. 1-8.

Agranovsky et al., "Injectivity Sets for the Radon Transform Over Circles and Complete Systems of Radial Functions", pp. 1-33.

Agranovsky et al. "Geometry of Stationary Sets for the Wave Equation in $R^n$. The Case of Finitely Supported Initial Data", pp. 1-24.

Helgason, S., *The Radon Transform*, Birkhauser (1980), Ch. I and II (pp. 1-92).

\* cited by examiner

METHOD AND SYSTEM OF THERMOACOUSTIC COMPUTED TOMOGRAPHY

BACKGROUND OF THE INVENTION

The present invention relates generally to diagnostic imaging and, more particularly, to a method and system of thermoacoustic computed tomography (TCT) such that unmeasured TCT data is determined from measured TCT data.

It is generally well known that wave propagation and integral geometry are the physical and mathematical underpinnings of most diagnostic imaging modalities. To date, most of these standard modalities have been predicated upon the measurement of the same type of output energy as was input to the system. For example, ultrasound diagnostic systems transmit and receive ultrasonic waves and, from those ultrasonic waves, are capable of generating a diagnostic image. CT systems are predicated upon the transmission and reception of x-ray or gamma ray radiation. In conventional CT systems, x-rays are projected toward an imaging subject and the attenuation of those x-rays caused by the subject is measured and processed to reconstruct a diagnostically valuable and probative image of the subject. Recently, however, hybrid imaging or diagnostic systems have been developed along with associated imaging techniques whereupon the measured output energy is different in form and type from the energy input to the system.

For instance, thermoacoustic tomography (TCT) is predicated upon and uses radio frequency (RF) energy projected at an imaging subject and measures emitted ultrasonic waves resulting from the application of the RF energy. Near infrared radiation is also non-ionizing and may also be used to heat tissue. TCT imaging involves the measurement of ultrasonic signals that are induced in the tissue of a subject whenever pulsed or continuous application of radiation is absorbed within the tissue, and the detection of resulting ultrasonic signals with transducers placed on or outside the imaging subject. More particularly, the ultrasonic transducers placed about the subject detect shock waves that are created in tissue when RF energy is absorbed and cause a heating and expansion of tissue. For example, it is known that cancerous masses absorb more RF energy than healthy tissue. As such, cancerous masses preferentially absorb RF energy, heat, and expand more quickly than neighboring healthy tissue thereby creating a shock wave which, when detected by an ultrasonic transducer, allows for detection of, or contrast between, cancerous or abnormal tissues and healthy tissues. Therefore, assuming a constant sound speed, the sound or ultrasonic waves, detected at any point in time after application of the RF energy, are generated by inclusions or abnormal masses lying on a sphere of radius centered at a particular transducer. This is particularly illustrated in FIG. 1.

Turning to FIG. 1, a sphere 10 is shown with an imaging object 12 centrally placed therein. Placed at various positions along a lower portion 11 of the sphere are transducers 14 that will be used to detect or receive ultrasonic waves created within the imaging object as a result of the application of electromagnetic or RF energy. Further shown in FIG. 1 is an inadmissible transducer location generally referenced 16. The transducer location 16 is inadmissible given the imaging object's positioning within sphere 10. That is, in the example of application of TCT imaging to image a breast, the patient is placed face down on an imaging table such that the patient's breast is positioned within sphere portion 11. Therefore, it is clear that the breast is positioned within the lower hemisphere 11 of sphere 10 whereas the top portion 13 of sphere 10, which is shown in phantom, is occupied by portions from the patient on which data is be collected. As such, it is not possible to use or place a transducer at the referenced location 16 to collect data from object 12.

With TCT imaging, inversion of a generalized Radon transform is required because integrals of the tissue's RF absorption coefficient are measured over surfaces of the sphere. The data measured at the admissible transducer locations 14 is therefore an integral of the RF absorbtivity function over data arcs 15, 17, 18 in dimension N=3, given the three illustrated admissible transducer locations shown in FIG. 1. In other words, integrals along the arcs that would be associated with transducer location 16 cannot be directly measured with a transducer at location 16. The non-measurable arcs associated with transducer location 16 are shown as dashed arcs 19.

The inability to directly measure the data associated with a dedicated transducer at location 16 is problematic for a number of reasons. For instance, a lesion, cancerous mass, or other tissue abnormality that is the target of the diagnostic procedure may be within the realm of detection associated with the inadmissible transducer location 16 and, as such, is not sufficiently detected with transducer's position at the admissible transducer locations. In addition, current TCT imaging reconstruction techniques use filtering and backprojecting of only the data that is directly measured. As a result, using only the measured data may cause low frequency shading in the reconstructed image for relatively uniform imaging objects. Additionally, objects with high frequency content may suffer more severe artifacts when data or transducer locations go unmeasured.

It would therefore be desirable to design a method and system of TCT imaging whereupon data from otherwise directly unmeasurable transducer locations may be determined to improve not only image quality, but also sensitivity of a TCT data acquisition to an imaging object.

BRIEF DESCRIPTION OF THE INVENTION

The present invention is directed to a method and system of TCT imaging whereupon data associated with unmeasured or inadmissible transducer locations is determined from data acquired at measured or admissible transducer locations such that the aforementioned drawbacks are overcome. The invention analyzes measured TCT data associated with several transducer locations to provide an estimate of unmeasured data so as to complete a full data set for image reconstruction. In this regard, by measuring TCT data at many points on the surface of a hemispherical bowl or sphere in which an imaging object is placed, mathematical coefficients may be determined for the TCT data as a function of transducer location. From these coefficients, the unmeasured transducer locations may be evaluated such that data associated with the unmeasured transducer locations may be estimated and utilized for image reconstruction to improve image quality as well as improve the diagnostic sensitivities or capabilities of the TCT system.

Therefore, in accordance with one aspect of the present invention, a method of diagnostic imaging includes the step of acquiring a first set of TCT data from a first portion of a measurement surface. The method further includes the step of determining a second set of TCT data for a second portion of the imaging object from the first set of TCT data, the second portion being different from the first portion.

In accordance with another aspect of the present invention, a TCT imaging system includes an energy source configured to project thermal inducing expansion energy to an imaging object. The imaging system also includes one or more sensors configured to acquire ultrasonic data from the imaging object caused by induced thermal expansion in the imaging object. A computer is provided and programmed to derive, from the acquired data, unacquired data for the imaging object.

According to another aspect, the present invention includes a computer readable storage medium having a computer program stored thereon and representing a set of instructions that, when executed by a computer configured to acquire TCT data from the imaging object causes the computer to determine coefficients of a polynomial expression that is relative to a position of a transducer about an imaging object. The set of instructions further causes the computer to determine, from of the determined coefficients, TCT data corresponding to a desirable transducer location about the imaging object not having a transducer.

In accordance with yet another aspect, the present invention includes a method of imaging a breast that includes projecting high frequency energy toward a breast to induce thermal expansion of tissue in the breast and receiving ultrasonic emissions from a first portion of a measurement surface resulting from the thermal expansion. The method also includes generating a first TCT dataset from the ultrasonic emissions and deriving a second TCT dataset from the first TCT dataset.

Various other features, objects and advantages of the present invention will be made apparent from the following detailed description and the drawings.

BRIEF DESCRIPTION OF THE DRAWINGS

The drawings illustrate one preferred embodiment presently contemplated for carrying out the invention.

In the drawings.

DETAILED DESCRIPTION OF THE PREFERRED EMBODIMENT

Figure 2:
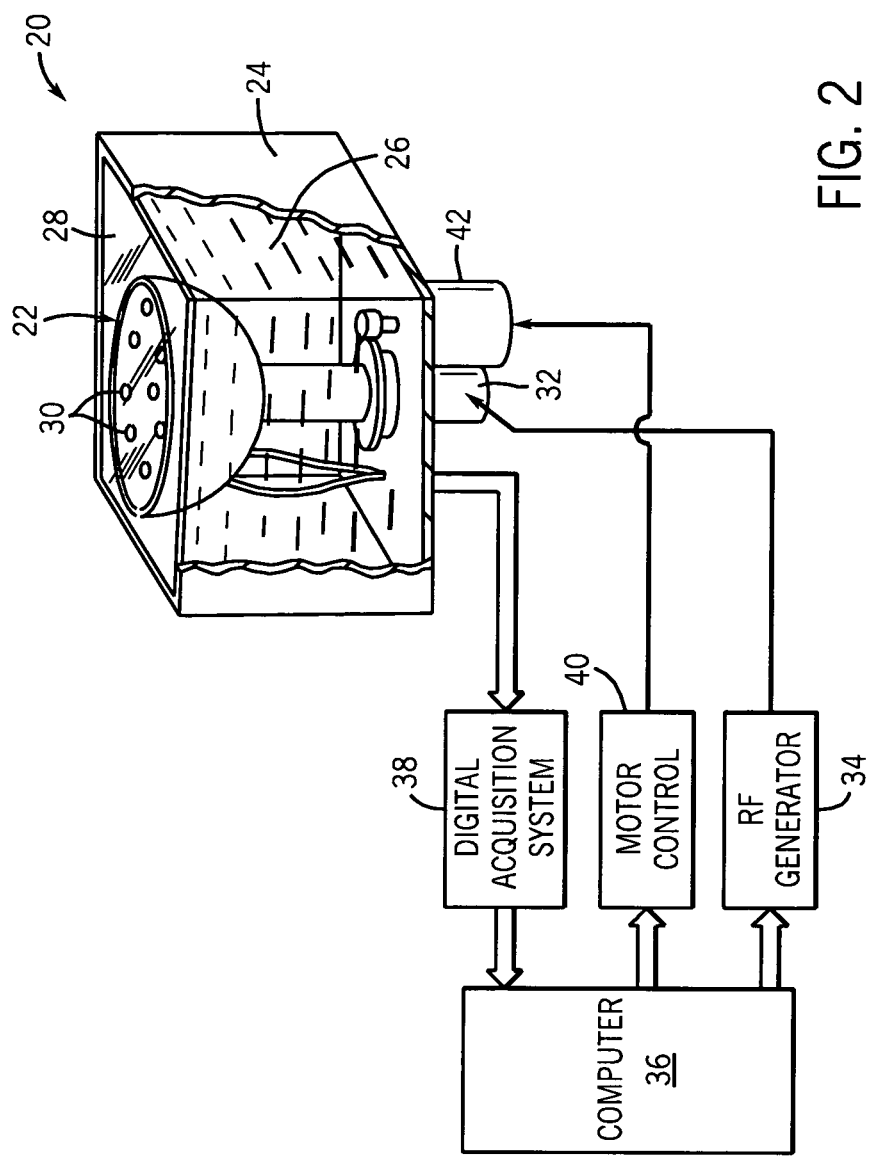
FIG. 2 is a schematic view of a TCT breast scanner in which the present invention is applicable.

Referring now to FIG. 2, a TCT breast scanner or mammography system 20 is schematically illustrated. While the present invention will be described with respect to a TCT system designed to acquire data in accordance with a mammography, one skilled in the art will appreciate that the present invention is equivalently applicable with TCT systems designed for other purposes. In one embodiment, the TCT system 20 includes an imaging bowl 22 designed to receive a human breast for TCT data acquisition. The imaging bowl 22 is preferably located within an imaging tank 24 that includes fluid or other media having dialectic and ultrasonic properties which are close to that of typical breast tissue at RF frequencies. Additionally, it is preferred that the fluid contained within tank 24 have acoustic properties similar to that of breast tissue, such as water, alcohol, or mineral oil. In one embodiment, the breast is placed directly within media 26 or, in an alternate embodiment, media 26 may be secured within tank 24 by a sheet 28 of pliable material. It is preferred that pliable sheet 28 have a relatively thin thickness and is used to provide good mechanical contact and acoustic coupling between the breast and media 26 in tank 24.

As mentioned previously, TCT imaging is predicated upon the projection of RF energy toward an imaging object such that thermal expansion occurring as a result of the reception of the radio waves causes shock waves in the imaging object that may be detected by ultrasonic transducers. It is contemplated that infrared or near-infrared energy may equivalently be used to induce thermal expansion in tissue of the imaging object. In this regard, imaging bowl 22 includes a number of ultrasonic transducers 30 that are integrated or otherwise formed therewith. To facilitate the transmission of RF or other high frequency energy toward the imaging object, a cylindrical acoustic wave guide 32 is connected to an RF generator 34 and operates as an antenna for irradiating the imaging object. In a preferred embodiment, RF generator 34 is controlled by computer 36 in such a manner as to provide short duration pulses of radiation to the breast or imaging object. Each pulse or burst of radiation causes localized heating and expansion in the energy object. The tissue heating energy may be projected in several fashions. For example, the energy may be projected impulsively in time and uniformly in space. Other examples include: periodically in time and uniformly in space, impulsively in time and selectively in space, and periodically in time and selectively in space. Based on the absorbtive characteristics of tissue in the imaging object, neighboring tissues may be distinguished from one another. For example, tumorous tissue is believed to expand relatively more rapidly and extensively than neighboring healthy tissue thereby creating an acoustic wave that will propagate through the tissue. These acoustic waves have acoustic frequencies ranging from very low to approximately the reciprocal of the electromagnetic pulse length. One skilled in the art will appreciate that the acoustic waveforms produced by RF irradiation within the breast travel through tissue at a velocity of sound propagation which is approximately 1.5 mm per microsecond. Fluid 28 fills the tank 24 to provide good ultrasound coupling between the tissue and transducers. One skilled in the art will recognize that the choice of fluid determines not only ultrasound coupling but also RF penetration properties. Furthermore, other embodiments may not require a fluid-filled tank. For instance, transducers might be placed directly on the patient's skin and RF may propagate through air, as is done in clinical magnetic resonance imaging systems.

TCT system 20 is designed to operate with several different RF frequencies, but frequencies in the range of 200 to 600 MHz are preferred. At these frequencies, energy penetration is sufficient, absorption is adequate, and the differential absorption between different types of tissue is distinguishable. Further, it has been shown that cancerous breast tissue absorbs two to five times as much RF energy than normal breast tissue once stimulated with frequencies in the range of 300 to 500 MHz. Additionally, it is believed that signal-to-noise ratio (SNR) is optimized in imaging water-containing tissues at frequencies near 434 MHz.

Transducers 30, as noted above, detect acoustic or ultrasonic waves that are generated within the imaging object by short irradiation pulses from RF generator 34. The acoustic waves travel from emission sites within the imaging object at the velocity of sound in tissue. It is preferred that the transducers be constructed so as to be most sensitive to sonic frequencies nominally below the maximum frequency stimulated by the irradiation pulse described above. Furthermore, for a three-dimensional embodiment of this invention, the transducers should have isotropic sensitivity to incoming pressure waves. On the other hand, for a two-dimensional embodiment, transducers should be focused to receive only waves originating within the imaging plane. The transducers 30 are electrically connected to a digital acquisition system 38 whereupon the data is input to computer 36 for image reconstruction.

It is contemplated that imaging bowl 22 as well as transducers 30 may be rotated during data acquisition. As such, TCT system 20 includes a motor control 48 that is driven by computer 36 so as to rotate imaging bowl 22 during the acquisition of TCT data. It is contemplated, however, that rotation of imaging bowl 22 may not be desirable for some TCT imaging protocols.

As described above, imaging bowl 22 is constructed to have a hemispherical shape. As such, transducers may only be positioned or integrally formed about the hemispherical surface of the imaging bowl. Accordingly, data may only be directly acquired from the imaging object at the several transducer locations along the hemispherical surface of the imaging bowl. As a result, it is not possible to directly acquire data from those portions of the imaging object that would correspond to transducer locations of the mirrored, albeit imaginary, portion of imaging bowl 22. As noted above, this lack of data acquisition may affect the diagnostic value of the reconstructed image as well as the image's quality.

Accordingly, the present invention includes an imaging technique for deriving data that would otherwise have been acquired at inadmissible transducer locations. That is, the imaging technique is designed to derive the TCT data that cannot be readily acquired. The present technique is able to determine the unmeasured data by enforcing consistency conditions upon the actual TCT data acquired. As will be described more fully below, TCT consistency conditions, which are similar to the Helgason-Ludwig moment conditions of CT data, imply that for each transducer location, the TCT data may expand in a polynomial series, such a Legendre series, where only the non-zero coefficients are the even coefficients and that these coefficients are themselves polynomials of known degree in the elements of transducer location. By measuring TCT data at many points on the surface of the hemispherical imaging bowl, the exact form of each Legendre or other polynomial coefficient may be computed as a function of transducer location. Once these coefficients are known, the polynomial expansions are evaluated at unmeasured transducer locations on what would correspond to the upper hemisphere of the imaging bowl. With this imaging technique, artifact levels in the reconstructed image or images of the imaging object are reduced without sacrificing SNR. The mathematical underpinnings of determining or otherwise extrapolating data corresponding to the unmeasured transducer locations from the data of the measured transducer locations are set forth below.

If $p \in S^{(n-1)}$ and $f \in C_o^\infty(B_1)$, where $B_1$ is a unit ball or object centered at the origin of unit sphere S, TCT data may then be defined as the integral of f over spheres centered on the surface of the unit sphere as set forth in the following expression:

$$R_{TCT}f(p,r) = r^{n-1} \int_{o \in S^{(n-1)}} f(p+ro)\,do \quad \text{(Eqn. 1)}$$

where p denotes the center of spheres of radius r and |p|=1. TCT data is estimated or otherwise determined for inadmissible transducer locations and input into an inversion formula that computes f(x) from measurements of $R_{TCT}f(p,r)$ data for all transducer locations. From the estimated data and the inversion formula it is therefore possible to recover the absorptivity function. It is desirable to describe range or consistency conditions for $R_{TCT}$ which may be used to extrapolate unmeasured data for an inadmissible transducer location, $p \in S_+^2$, from measurements taken by transducers at actual transducer locations. In this regard, an inadmissible transducer location may be considered as a data derivation location.

One skilled in the art will appreciate that the definition of $R_{TCT}$, as provided in Eqn. 1, is restrictive, in that it permits only measurement of integrals centered on the surface of the unit sphere. This restriction makes computation of the adjoint and inverse operators simple. As in classical CT, the TCT adjoint operation is backprojection as demonstrated below. With TCT, however, $R^*_{TCT}$ is not applied directly to the data as is done in standard CT. The use of the TCT adjoint will now be compared with the standard Radon adjoint.

The TCT adjoint may be defined for any value, n, by the following expression:

$$R^*_{TCT}g(x) = \int_{|p|=1} g(p, |x-p|)\,dp. \quad \text{(Eqn. 2)}$$

A number of techniques may be used to derive exact inversion formulae for a complete data case. Fourier-Bessel expansion is one technique and results in a solution written as an infinite series. Another technique may be characterized as a TCT analog of p-filtered layergram inversion, as set forth in the following equation for n=3:

$$f(x) = \frac{1}{16\pi^3} \Delta_x \left( \int_{|p|=1} \frac{1}{|x-p|} R_{TCT}f(p, |x-p|)\,dp \right). \quad \text{(Eqn. 3)}$$

One skilled in the art will appreciate that the heretofore described inversion formula may be evaluated for odd values of n, i.e. 3, 5, 7, . . . . For n=2, a Norton-based inversion formula may be derived. It should be noted that the adjoint acts upon weighted data. By defining a weighting operator as:

$$Wg(p,s) = \frac{1}{s}g(p,s), \quad \text{(Eqn. 4)}$$

then the inversion formula for n=3 may be written as:

$$f(x) = \frac{1}{16\pi^3}\Delta_x(R^*_{TCT}WR_{TCT}f)(x). \quad \text{(Eqn. 5)}$$

Eqn. 5 differs from a standard codim-1 Radon inversion formula in the appearance of the weighting function, W. As is known, standard Radon data is not weighted prior to backprojection, as illustrated in the following equation:

$$f(x) = \frac{-1}{8\pi^2}\Delta_x(R^*Rf)(x). \quad \text{(Eqn. 6)}$$

It should be noted that for reconstruction points below the equator of a unit sphere, the TCT inversion formula defined by Eqn. 6 weights data from admissible transducer locations on the lower half ($S_-$) of the unit sphere more heavily than data from the upper half ($S_+$).

A partial characterization of the TCT transform is followed by a discussion of its implications. A first step in characterizing the range of $R_{TCT}$ is to take the even extension with respect to the scalar variable r of TCT data as defined by Eqn. 1, which may be written as:

$$R_{TCT}f(p,r) = R_{TCT}f(p,-r) \qquad \text{(Eqn. 7)}.$$

From this, it can be shown that TCT data is subject to consistency conditions. The subjection of TCT data to consistency conditions is shown in the following moments equation:

$$Mom_k(p) \equiv \int_{R_+} r^k R_{TCT}f(p,r)dr = \int_{x \in R^3} |x-p|^k f(x)dx. \qquad \text{(Eqn. 8)}$$

In particular, moments of even order are polynomials with respect to source (transducer) position, $p \in S^2$ and may be defined as:

$$Mom_{2k}(p) = \int_{R''} (|x|^2 - 2x \cdot p + |p|^2)^k f(x) dx = Q_k(p), \qquad \text{(Eqn. 9)}$$

where $Q_k$ is an inhomogeneous polynomial of degree 2 k in the elements p. When p is restricted to the surface of a sphere, $|p| \equiv c$, then $Q_k$ is of degree k.

As is known for standard x-ray CT, enforcing the range conditions by projecting data orthogonally onto the range of the Radon transform does not improve image quality of p-filtered reconstructions. This is simply because the very first step in p-filtered reconstruction is backprojection, i.e., application of the adjoint operator. Because the range of an operator is always orthogonal to the nullspace of its adjoint, errors which are orthogonal to the range of the Radon transform are automatically annihilated by the backprojector. That is, enforcing consistency conditions annihilates errors orthogonal to the range of the $R_{TCT}$ transform.

As will be described, $R_{TCT}$ can be computed for inadmissible transducer locations from measurements made at admissible transducer locations. TCT data can be expanded in terms of Legendre polynomials for each transducer location, p, because of the assumption that supp $f \subset B_1$. The necessary range conditions discussed above imply that these expansions take a very special form. One skilled in the art will appreciate that the TCT data may be expressed according to other polynomial expressions and the present invention is applicable therewith. TCT data can be expanded as a Legendre series for each transducer location p with only even terms as set forth by:

$$R_{TCT}f(p,r) = \sum_{k=0}^{\infty} c_k(p) P_{2k}(r). \qquad \text{(Eqn. 10)}$$

Furthermore, the coefficients, $c_k(p)$, are inhomogeneous polynomials of degree 2 k in terms of the elements of p. Restricting $|p| \equiv c$ implies deg $c_k = k$. This is illustrated in the following proof. Firstly, units of r are taken to be the diameter of the object $B_1$. Moreover, because the even extension with respect to r was taken in Eqn. 7, all odd terms in the expansion are identically zero and therefore the coefficients of even terms are defined as:

$$c_k(p) = \int_{r=-1}^{1} P_{2k}(r) R_{TCT} f(p,r) dr. \qquad \text{(Eqn. 11)}$$

To characterize the coefficients $c_k(p)$, it is noted that $P_{2k}$ is a linear combination of even powers of $r^2$. By Eqn. 9, $c_k(p)$ is an inhomogeneous polynomial of degree 2 k and defined:

$$c_k(p) = \sum_{|\alpha| \leq 2k} c_k^\alpha p^\alpha, \qquad \text{(Eqn. 12)}$$

where a Laurent-Schwartz notation is used to define $\alpha \in N^3$ and $p^\alpha = p_1^{\alpha_1} p_2^{\alpha_2} p_3^{\alpha_3}$. As will be described, Eqn. 12 will be used to derive $R_{TCT}$ for inadmissible transducer locations relative to an imaging object.

Data measured or otherwise determined at admissible transducer locations, $R_{TCT}$, can be derived or otherwise determined for inadmissible transducer locations. When $R_{TCT}$ and therefore, $c_k(p)$, are known on $\forall p \in S_-^2$ the coefficients $\{c_k^\alpha\}$ can be estimated. With these coefficients, Eqns. 10 and 12 can be evaluated for data derivative locations $p \in S_+^2$.

Figure 1:
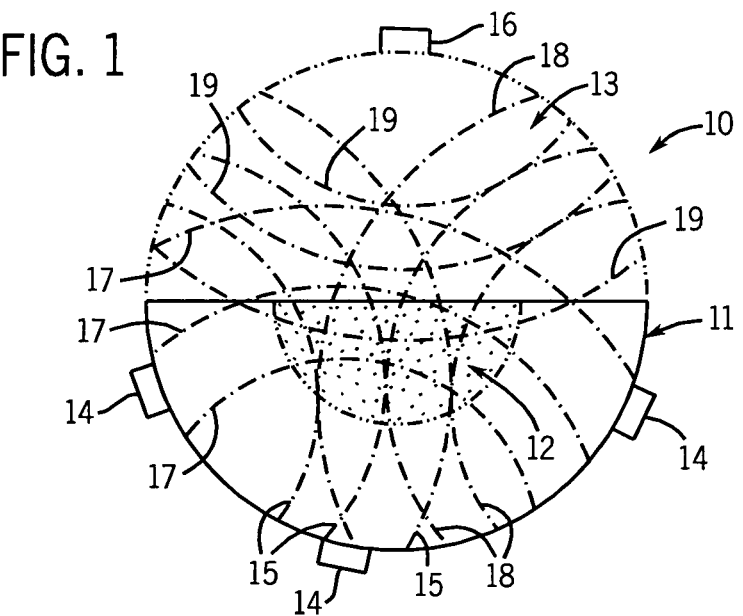
FIG. 1 is a schematic representation of a TCT imaging system for which the present invention is applicable illustrating examples of admissible and inadmissible transducer locations for TCT data acquisition relative to an imaging object.
Figure 3:
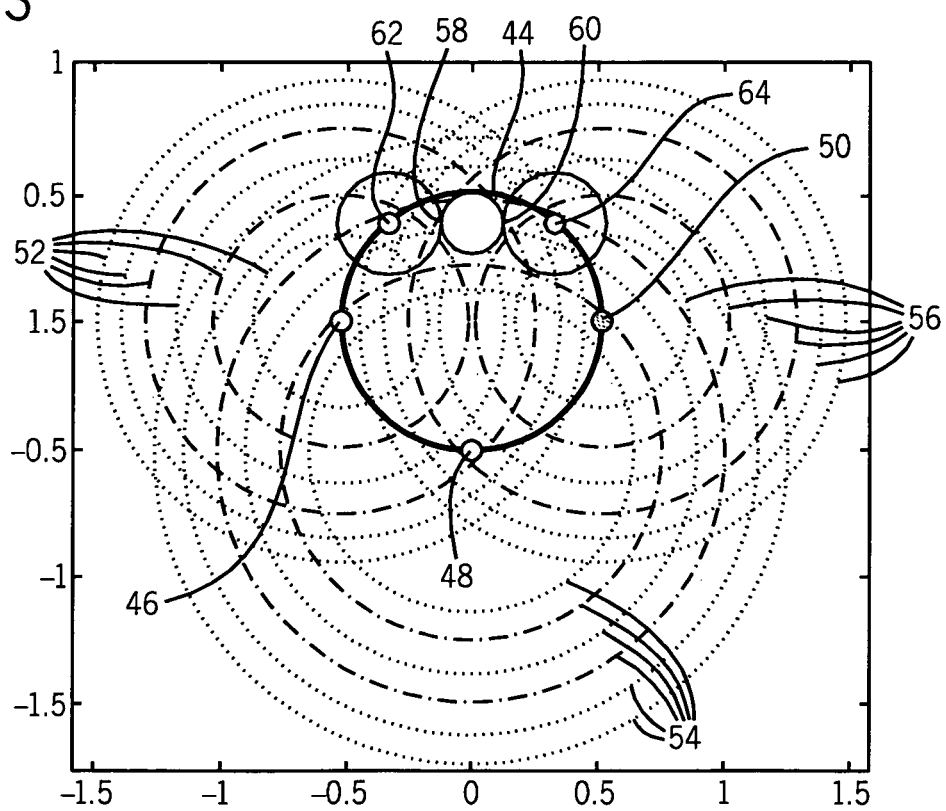
FIG. 3 is a schematic of TCT principles for imaging of an object.

Set forth below is an example of determining or deriving TCT data from measured data with a simple phantom for immeasurable transducer locations. The imaging object 44 is characterized as an indicator function $$f = \chi_{|x-(0,0,3/8)| < \frac{1}{8}}(x)$$

as shown in FIG. 3. Data is measured for transducer locations 46-50. As shown, none of the measured data, as illustrated by the arcs/spheres 52-56 associated with transducer locations 46-50, respectively, directly includes data for the vertical edges 58 and 60 of the inclusion 44. In contrast, data measured with transducers located at $p_o = (\sqrt{7}/8, 0, \frac{3}{8})$ 62 and 64 would detect the vertical edges of inclusion 44.

This phantom is invariant under rotation about the z-axis, so each of the coefficients is a polynomial of a single variable:

$$R_{TCT}f(p_1, p_2, p_3, r) = R_{TCT}f(p_3, r) \qquad \text{(Eqn. 13)},$$

which implies $$c_k(p_1, p_2, p_3) = \sum_{\alpha=0}^{k} c_k^\alpha p_3^\alpha, \qquad \text{(Eqn. 14)}$$

and p lies on the sphere of diameter one-half, $|p| = \frac{1}{2}$. As such, the partial scan data may be defined as $p_3 \in [-\frac{1}{2}, 0]$. Rescaling makes $c_k$ a polynomial over the interval $[-1,1]$. Letting $$p_{new} = 4p_3 + 1, \qquad \text{(Eqn. 15)}$$

then $$c_k = c_k(p_{new}) = \sum_{\alpha=0}^{k} d_k^\alpha \frac{P_\alpha(p_{new})}{\sqrt{2/(2\alpha+1)}}. \qquad \text{Eqn. (16)}$$

For each transducer location, $p_{new}$, the data $R_{TCT}(p_{new}, r)$ is sampled with high frequency in r. In the results presented below, it was assumed continuous sampling with respect to r and $c_k(p_{new})$ was determined analytically from Eqn. 10. Sampling $p_3 \in [-\frac{1}{2}, 0]$ was carried out so that $p_{new}$ are Gaussian quadrature nodes of order 24. The results were computed using 32 and 40 significant digits, respectively. Numerically integrating Ck against $$\frac{P_\beta(p_{new})}{\sqrt{2/(2\beta+1)}}$$

for $\beta = 0, 1, 2, \ldots, k$ computes $d_k^\beta$.

Plugging the coefficients $d_k^\alpha$ back into Eqns. 14 and 10 allows for evaluation at the unmeasured transducer locations $p_o = (\sqrt{7}/8, 0, \frac{3}{8})$ which rescales to give $p_{o,new} = 4 \cdot \frac{3}{8} + 1 = 5/2$, and therefore:

$$R_{TCT}f(p_{o,new}, r) = \sum_{k=0}^{\infty} c_k(p_{o,new}) P_{2k}(r) \qquad \text{(Eqn. 17)}$$

$$= \sum_{k=0}^{\infty} \sum_{\alpha=0}^{k} d_k^\alpha \frac{P_\alpha(5/2)}{\sqrt{2/(2\alpha+1)}} P_{2k}(r).$$

The present invention is directed to a TCT imaging technique whereupon data from immeasurable transducer locations data is determined from measured TCT data. The example presented above corroborates this theory and indicates that high-order approximations to unmeasured data is possible. Moreover, it can be reasonably expected that low-order estimates of $R_{TCT}$ for inadmissible transducer locations $p \in S_+$ will reduce partial scan artifacts in the admissible reconstruction region, i.e. data from admissible transducer locations.

Therefore, in accordance with one embodiment of the present invention, a method of diagnostic imaging includes the step of acquiring a first set of TCT data from a first portion of a measurement surface. The method further includes the step of determining a second set of TCT data for a second portion of the imaging object from the first set of TCT data, the second portion being different from the first portion.

In accordance with another embodiment of the present invention, a TCT imaging system includes an energy source configured to apply energy to an imaging object designed to cause thermal expansion and/or contraction in the imaging object. The imaging system also includes one or more sensors configured to acquire ultrasonic data from the imaging object caused by thermal expansion/contraction in the imaging object. A computer is provided and programmed to derive, from the acquired data, unacquired data for the imaging object.

According to another embodiment, the present invention includes a computer readable storage medium having a computer program stored thereon and representing a set of instructions that, when executed by a computer configured to acquire TCT data, causes the computer to determine coefficients of a polynomial expression with respect to transducer position. The set of instructions further causes the computer to evaluate said polynomial and determine TCT data corresponding to a desirable transducer location about the imaging object not having a transducer.

In accordance with yet another embodiment, the present invention includes a method of imaging a breast that includes projecting RF energy toward a breast to induce thermal expansion of tissue in the breast and receiving ultrasonic emissions from a first portion of a measurement surface resulting from the thermal expansion. The method also includes generating a first TCT dataset from the ultrasonic emissions and deriving a second TCT dataset from the first TCT dataset.

The present invention has been described in terms of the preferred embodiment, and it is recognized that equivalents, alternatives, and modifications, aside from those expressly stated, are possible and within the scope of the appending claims.

What is claimed is:

1. A thermoacoustic computed tomography (TCT) imaging system comprising:
   an energy source configured to apply energy to an imaging object to induce thermal expansion in the imaging object;
   one or more sensors positioned at one or more respective positions and configured to acquire ultrasonic data from the imaging object caused by RF energy-induced thermal expansion in the imaging object; and
   a computer programmed to derive, from the acquired data, unacquired data for the imaging object for one or more locations inadmissible for sensor positioning due to a positioning of the imaging object.

2. The TCT imaging system of claim 1 wherein the computer is further programmed to derive the unacquired data by evaluating coefficients of a polynomial expression of the acquired data.

3. The TCT imaging system of claim 2 wherein the computer is further programmed to determine the polynomial expression relative to sensor position about the imaging object.

4. The TCT imaging system of claim 1 wherein the energy to induce thermal expansion includes one of RF energy, infrared energy, and near-infrared energy.

5. The TCT imaging system of claim 4 configured to determine a presence of an abnormality in breast tissue.

6. The TCT imaging system of claim 5 further comprising a hemispherical shaped imaging tank having a fluid disposed therein, the fluid having dielectric and ultrasonic properties similar to that of breast tissue.

7. The TCT imaging system of claim 6 wherein the one or more sensors are placed along an external surface of the hemispherical shaped tank.

8. A computer readable storage medium having a computer program stored thereon and representing a set of instructions that when executed by a computer causes the computer to:
   determine coefficients of a polynomial expression that is relative to a position of a transducer about an imaging object;
   acquire thermoacoustic computed tomography (TCT) data from the imaging object;
   from the coefficients, determine TCT data corresponding to a desirable transducer location about the imaging object that is inadmissible to a TCT transducer; and
   generate an image using at least the TCT data determined from the coefficients.

9. The computer readable storage medium of claim 8 wherein the set of instructions further causes the computer to impose consistency conditions on acquired TCT data such that coefficients of even terms of the polynomial expression are evaluatable to determine TCT data corresponding to the desirable transducer locations.

10. The computer readable storage medium of claim 8 wherein the set of instructions further causes the computer to reduce partial scan artifacts in acquired TCT data.

11. The computer readable storage medium of claim 8 wherein the polynomial expression is a Legendre polynomial.

12. A method of imaging a breast comprising the steps of:
- projecting high frequency energy toward a breast to induce thermal expansion of tissue in the breast;
- receiving ultrasonic emissions at a first set of transducer locations from a first portion of the breast resulting from the thermal expansion;
- generating a first thermoacoustic computed tomography (TCT) dataset from the ultrasonic emissions;
- deriving a second TCT dataset from the first TCT dataset, the second TCT dataset including data for transducer locations mirrored from the first set of transducer locations; and
- generating an image using at least the second TCT dataset.

13. The method of claim 12 wherein the second TCT dataset corresponds to a second portion of the breast from which ultrasonic emissions were not directly received.

14. The method of claim 12 wherein the high frequency energy includes one of RF, infrared, and near-infrared energy.

* * * * *